United States Patent [19]
Qian et al.

[11] Patent Number: 5,654,465
[45] Date of Patent: Aug. 5, 1997

[54] PROCESS FOR THE PRODUCTION OF CYANOCINNAMAMIDES

[75] Inventors: Zhenrong Qian, Randolph; Heng Su, Whippany; Chempolil Thomas Mathew, Randolph, all of N.J.

[73] Assignee: AlliedSignal Inc., Morris County, N.J.

[21] Appl. No.: 729,213

[22] Filed: Oct. 15, 1996

[51] Int. Cl.$^6$ .................. C07C 253/30; C07D 241/04
[52] U.S. Cl. ............................... 558/373; 544/387
[58] Field of Search .................. 558/373; 544/387

[56] References Cited

U.S. PATENT DOCUMENTS

| | | | |
|---|---|---|---|
| 2,583,194 | 1/1952 | Weisler | 558/373 |
| 2,623,060 | 12/1952 | Cragoe, Jr. | 260/465 |
| 2,832,790 | 4/1958 | Howard, Jr. | 260/326.3 |
| 3,960,923 | 6/1976 | DeSimone | 558/373 |

FOREIGN PATENT DOCUMENTS

| | | |
|---|---|---|
| 0 226 541 | 6/1987 | European Pat. Off. . |
| 0 430 023 | 6/1991 | European Pat. Off. . |

OTHER PUBLICATIONS

E.J. Cragoe, Jr. et al. *J. Org. Chem.*, vol. 15, p. 381, (1950).

H.T. Openshaw and N. Whittaker. *J. Amer. Chem. Soc.*, 1963, p. 1461.

H.T. Openshaw and N. Whittaker. *J. Chem. Soc.*, 1969, p. 89.

B. Singh. *Tetrahedron Letters*. No. 4, pp. 321–322, 1971.

H. Yazawa et al. *Tetrahedron Letters*. No. 46, pp. 3995–3996, 1974.

Y. Sumida and O. Vogl. *Polymer Journal*, vol. 13, No. 6, pp. 521–536 (1981).

*Primary Examiner*—Peter O'Sullivan
*Attorney, Agent, or Firm*—Lois A. Gianneschi

[57] ABSTRACT

This invention provides a process for producing cyanocinnamamides. More particularly, the invention provides a process for condensing an cyanoacetamide with a carbonyl-containing compound to produce cyanocinnamamides in good yield.

36 Claims, No Drawings

PROCESS FOR THE PRODUCTION OF CYANOCINNAMAMIDES

FIELD OF THE INVENTION

This invention relates to a process for producing cyanocinnamamides. More particularly, the invention provides a process for condensing a cyanoacetamide with a carbonyl-containing compound to produce cyanocinnamamides in good yield.

BACKGROUND OF THE INVENTION

Cyanocinnamamides are known to be useful as ultraviolet stabilizers for polymers including for polycarbonates, polyesters, and polyamides. A number of processes for production of cyanocinnamamides are known. For example in one process, a benzophenone is condensed with a cyanoacetate to form the corresponding cyanocinnamate ester, followed by the transformation of the ester into the acid by saponification. Acid chloride is prepared by the reaction of the acid with thionyl chloride, followed by reaction with an amine to form the amide. In another process, after condensation of the cyanoacetate and benzophenone, the cyanocinnamic acid converted by the saponification is directly converted to the corresponding amide by reaction with its isocyanate.

These processes are disadvantageous in that they are multi-step processes and involve difficult to handle intermediate compounds and reagents such as acid chloride, thionyl chloride, and isocyanate. Thus, a need exists for an efficient method for producing cyanocinnamamides that avoids some of the disadvantages of the known processes.

DETAILED DESCRIPTION OF THE INVENTION AND PREFERRED EMBODIMENTS

The process of the invention provides an efficient, economical process for producing cyanocinnamamide compounds in good yield. The process of the invention comprises contacting a cyanoacetamide with an effective amount of a carbonyl-containing organic compound, a catalytic amount of a condensation catalyst, and a sufficient amount of solvent under conditions suitable to form a cyanocinnamamide compound.

By cyanocinnamamide compound is meant compounds of the formula:

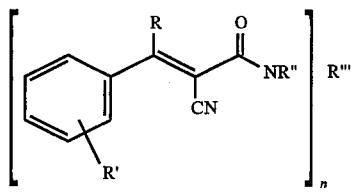

where n is 1 or 2, R is hydrogen or a $C_1$ to $C_6$ straight chained or branched alkyl, a $C_3$ to $C_7$ cycloalkyl, a $C_2$ to $C_{12}$ alkenyl, or a phenyl group unsubstituted or substituted with R', R' is a $C_1$ to $C_6$ straight chained or branched alkyl, a $C_1$ to $C_6$ alkoxy, a $C_1$ to $C_6$ thioalkyl, or a cyano, halogen, or $C_1$ to $C_2$ dialkylamino group, and when n=1, R" is hydrogen, and R'" is a $C_1$ to $C_6$ straight chained or branched alkyl, a $C_3$ to $C_7$ cycloalkyl, or a $C_2$ to $C_6$ alkenyl, and when n=2, R" is hydrogen and R'" is a $C_1$ to $C_{20}$ straight chained or branched alkylene, a $C_3$ to $C_7$ cycloalkylene, or $C_2$ to $C_{20}$ alkenylene and when R" is a methylene group then R'" is an ethylene group forming a six membered ring.

Cyanoacetamides useful in the process of the invention are of the formula:

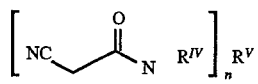

where n may be 1 or 2, and when n=1, $R^{IV}$ is hydrogen and $R^V$ is a $C_1$ to $C_6$ straight chained or branched alkyl, a $C_3$ to $C_7$ cycloalkyl, or a $C_2$ to $C_6$ alkenyl, and when n=2 $R^{IV}$ is hydrogen and $R^V$ is a $C_2$ to $C_{20}$ straight chained or branched alkylene, a $C_3$ to $C_7$ cycloalkylene, or a $C_2$ to $C_{20}$ alkenylene and when $R^{IV}$ is a methylene then $R^V$ is an ethylene group forming a six membered ring. Preferably, the cyanoacetamide is α,ω-hexamethylene bis-cyanoacetamide.

The cyanoacetamides useful in this invention may be conveniently synthesized by aminolysis of a cyanoacetic ester with an amine by any of the well known aminolysis processes. In general, the cyanoacetamide may be formed by aminolysis of an amine and an effective amount of a cyanoacetic ester of the formula:

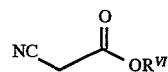

wherein $R^{VI}$ is a $C_1$ to $C_6$ straight chained or branched alkyl radical. The amine may be a monoamine of the formula $H_2NR^{VII}$ where $R^{VII}$ is a $C_1$ to $C_6$ straight chained or branched alkyl, $C_3$ to $C_7$ cyclo alkyl or a $C_2$ to $C_6$ alkenyl or a diamine that is piperazine or of the formula $H_2N(R^{VIII})NH_2$ wherein $R^{VIII}$ is a $C_2$ to $C_{20}$ straight chained or branched alkylene, a $C_3$ to $C_7$ cyclo alkylene, or $C_2$ to $C_{20}$ alkenylene radical. Preferably, a diamine, more preferably α,ω-hexamethylenediamine is used.

The amount of ester used is an amount effective to bring about the formation of the desired cyanoacetamide. Generally, about 1 to about 3, preferably about 1.5, molar equivalents of ester are used per molar equivalent of monoamine or about 2 to about 4, preferably about 3, molar equivalents of ester to equivalent of diamine. The cyanoacetamides may be formed readily in any suitable non-polar protic or aprotic solvent such as methanol, ethanol, toluene, xylenes or mixtures thereof. Preferably, an aprotic solvent, such as toluene or xylenes is used. The aminolysis may be carried out at room temperature although higher temperatures, from about 20° to about 110° C., may be useful depending on the structure of the amine or diamine. Pressure is not critical.

It has been discovered that, by contacting a cyanoacetamide with a carbonyl-containing organic compound in accordance with the process of this invention, a cyanocinnamamide compound may be produced simply and efficiently in good yield. By carbonyl-containing organic compound is meant a ketone or aldehyde. Ketones useful in the process of the invention include, without limitation, benzophenone, substituted benzophenone such as alkylbenzophenone, alkylthiobenzophenone, alkoxybenzophenone, cyanobenzophenone, halobenzophenone, N,N-dialkylaminobenzophenone, and acetophenone, substituted acetophenones such as alkylacetophenone, alkylthioacetophenone, alkoxyacetophenone, cyanoacetophenone, haloacetophenone, N,N-dialkylaminoacetophenone. Preferably, a substituted or unsubstituted, more preferably an unsubstituted, benzophenone is used. The molar equivalents of ketone to the cyanoacetamide or bis-cyanoacetamide used are from about 1:1 to about 4:1. Preferably about 1.2:1 molar equivalents of ketone to cyanoacetamide, or preferably 2.4:1 molar equivalents of ketone to bis cyanoacetamide, are used.

Alternatively, the condensation may be performed using an aldehyde. Useful aldehydes include, without limitation, benzaldehyde, substituted benzaldehydes including without limitation alkylbenzaldehyde, alkylthiobenzaldehyde, alkoxybenzaldehyde, cyanobenzaldehyde, halobenzaldehyde, N.N-dialkylaminobenzaldehyde. Preferably, benzaldehyde is used. The molar equivalents of aldehyde to the cyanoacetamide or bis-cyanoacetamide used are from about 1:1 to about 4:1. Preferably about 1.2:1 molar equivalents of aldehyde to cyanoacetamide, or preferably 2.4:1 molar equivalents of aldehyde to bis cyanoacetamide, are used.

In the process of the invention, the cyanoacetamide, ketone or aldehyde, and condensation catalyst are mixed in an amount of solvent sufficient to form a solution of about 5 to about 20 percent amide. The solvent may be toluene, xylenes, or mixtures thereof. Any suitable condensation catalyst may be used including, without limitation, a solution of from about 5 to about 30, preferably about 18, percent ammonium acetate in acetic acid. A catalytic amount of catalyst is used which generally is an amount sufficient to catalyze the condensation reaction between the cyanoacetamide and the carbonyl-containing compound. Preferably, about 0.6 molar equivalents of catalyst per cyanoacetamide equivalent is used.

The cyanoacetamide, ketone or aldehyde, and catalyst are mixed together and the mixture is heated with stirring to a temperature at which the solvent selected refluxes out the water formed in the condensation reaction. Reaction times will depend on the cyanoacetamide and ketone or aldehyde used. Generally, the reaction time will be from about 2 to about 30 hours, preferably from about 10 to about 25 hours.

Optionally, the cyaoncinnamamide compound formed may be purified by any convenient means. For example the cyanocinnamamide may be washed with methanol, ethanol, normal propanol, isopropanol, ethyl acetate, or the like and dried.

The invention will be clarified further by the following, non-limiting examples.

EXAMPLES

Example 1

420 g hexamethylenediamine (3.6 moles) in 550 g toluene were charged into a 5 L, three-necked, round-bottomed-flask equipped with a mechanical agitator and a condenser connected with a nitrogen line. 753.5 g methyl cyanoacetate (7.6 moles) were added to the flask and the mixture stirred at room temperature for 20 hours. The solid formed was filtered by suction with a medium sintered glass funnel to isolate the product. The crystalline product was rinsed with 4600 g fresh toluene and dried in an oven at 40° C. under vacuum. Hexamethylene bis-cyanoacetamide was obtained as 872 g white crystals in 98% yield and with amp at 150° C.

24 g of the hexamethylene bis-cyanoacetamide (0.096 mole), 52.4 g benzophenone (0.288 mole), 28.8 g 25% ammonium acetate in acetic acid solution with 269 g toluene were placed in a 1 L, four-necked, round bottomed flask fitted with a mechanical agitator, thermometer, addition funnel, and a Dean-Stark water separator mounted with a reflux condenser. The reaction mixture was heated at reflux for 28 h with 4 mL 25% ammonium acetate in acetic acid solution added from the addition funnel every two hours. The reaction content was then cooled to room temperature and the solid obtained by filtration was washed with water (100 mL) then methanol (110 g×2) at 50° C. After being dried, the product, hexamethylene bis-(2-cyano-3-phenyl) cinnamamide (45.2 g) was obtained as white crystals in 81.7% yield, mp 232°–233° C.

Example 2

7.4 g, 0.1 moles ethylenediamine in 200 mL toluene were charged into a 500 mL, three-necked, round-bottomed flask equipped with a mechanical agitator and a condenser connected with a nitrogen line. Methyl cyanoacetate, 20.8 g, 0.21 moles, were added to the flask and the mixture stirred at room temperature for 20 hours. The solid formed was filtered by suction with a medium sintered glass funnel and the product washed with 2×100 mL toluene and dried in an oven at 40° C. under vacuum. 18.47 g ethylene bis-cyanoacetamide were obtained as white crystals in 88.7% yield, mp 74°–78° C. The structure of the chemical was confirmed by NMR.

9.72 g, 0.05 mole, ethylenediamine bis-cyanoacetamide, 20.1 g, 0.11 moles benzophenone, 28.3 g, 18% ammonium acetate solution in acetic acid in 40 g toluene were reacted according to the procedure of Example 1. After drying, ethylene bis-(2-cyano-3-phenyl)cinnamamide was obtained as off-white crystals in 48% yield and the structure was identified by NMR.

Example 3

20.5 g, 0.2 moles 2,2,-dimethyl-1,3-propanediamine in 320 mL toluene were charged into a 500 mL, three-necked, round bottomed flask equipped with a mechanical agitator and a condenser connected with a nitrogen line. 42.0 g methyl cyanoacetate, 0.42 moles, were added to the flask and the mixture was stirred at room temperature for 20 hours. The solid formed was filtered by suction with a medium sintered glass funnel and the isolated, crystalline product rinsed with fresh toluene (2×100 mL) and dried in a 40° C. oven under vacuum. 2,2,-dimethyl- 1,3-propanediamine bis cyanoacetamide was obtained as 43.6 g white crystals in 92.3% yield and mp 149° C. The structure was confirmed by NMR.

10.5 g, 0.05 mole, 2,2,-dimethyl-1,3-propanediamine bis-cyanoacetamide, 20.1 g, 0.11 moles benzophenone, 28.3 g, 18% ammonium acetate solution in acetic acid in 40 g toluene were reacted according to the procedure of Example 1. After drying, 2,2,-dimethyl-1,3-propanediamine bis-(2-cyano-3-phenyl)cinnamamide was obtained as off-white crystals in 54% yield and the structure was identified by NMR.

Example 4

43 g, 0.5 moles piperazine in 260 g toluene were charged to a one liter, three-necked, round-bottomed flask equipped with a mechanical agitator and a condenser connected with a nitrogen line. 140 g, 1.4 moles methyl cyanoacetate were added to the flask and the mixture stirred at reflux, 74°–89° C., for 20 hours. Methanol formed in the reaction was removed by Dean-Stark distillation. The solid product formed was isolated by filtration with a medium sintered glass funnel. The product was washed with 2×100 g toluene and dried in an oven at 40° C. under vacuum. 106.2 g piperazine bis-cyanoacetamide was obtained in a quantitative yield, mp 238° C. The structure of the product was confirmed by NMR analysis.

11.1 g, 0.05 mole, piperazine bis-cyanoacetamide, 20.1 g, 0.11 moles benzophenone, 28.3 g, 18% ammonium acetate solution in acetic acid in 240 g toluene were reacted according to the procedure of Example 1. The reflux time was about 31 hours. After drying, 9.3 g piperazine bis-(2-cyano-3-phenyl)cinnamamide were obtained as off-white crystals with mp. 275° C. in 33.8% yield and the structure was identified by NMR.

Example 5

9.5 g, 0.08 moles hexamethylenediamine in 102 g toluene were charged into a 500 mL, three-necked, round bottomed-flask equipped with mechanical agitator and a condenser connected with a nitrogen line. 22.62 g, 0.20 moles ethyl cyanoactetate were added to the flask and the mixture stirred at room temperature for 20 h. The solid formed was filtered by suction with a medium sintered glass funnel to isolate the product. The crystalline product was rinsed with fresh toluene (60 g×2) and dried in an oven at 40° C. under vacuum. Hexamethylene bis-cyanoacetamide was obtained as white crystals (20.7 g) in quantitative yield and mp at 150° C.

25. g, 0.1 mole hexamethylene bis-cyanoacetamide, 40.1 g, 0.22 mole benzophenone, 56 g 18% ammonium acetate in acetic acid solution with 80 g toluene were placed in a 500 mL, three-necked, round bottomed flask with built-in baffles fitted with a mechanical agitator, thermometer, addition funnel, and Dean-Stark water separator mounted with reflux condenser. The reaction mixture was heated at reflux for 21 hours. Then the reaction content was cooled to room temperature and the solid product was filtered. The product was washed with methanol (11 g×2) at 50° C. After being dried, the product hexamethylene bis-(2-cyano-3-phenyl)cinnamamide (5.2 g) was obtained as white crystals in 81.7% yield, mp 232°–233° C.

Example 6

14.4 g, 0.1 moles octamethylenediamine in 300 mL toluene were charged into a 500 mL, three-necked, round-bottomed flask equipped with a mechanical agitator and a condenser connected with a nitrogen line. 20.8 g, 0.21 moles methyl cyanoacetate were added to the flask and the mixture stirred at room temperature for 20 hours. The solid formed was filtered by suction with a medium sintered glass funnel to isolate the product. The crystalline product was rinsed with fresh toluene, 2×100 mL, and dried in an oven at 40° C. under vacuum. Ethylene bis-cyanoacetamide was obtained as 25.4 g of white crystals in 91.4% yield. mp 136° C. The structure of the chemical was confirmed by NMR.

26.0 g, 0.1 mole, octamethylene bis-cyanoacetamide, 40.1 g, 0.22 moles benzophenone, 56 g, 18% ammonium acetate solution in acetic acid in 80 g toluene were reacted according to the procedure of Example 1. After drying, 45.4 g octamethylene bis-(2-cyano-3-phenyl)cinnamamide were obtained as white crystals in 70.6% yield, mp 249° C.

Example 7

8.4 g, 0.1 moles of 2-cyanoacetamide and 20 g, 0.11 moles of benzophenone in 80 g toluene were charged to a four-necked, 500 mL flask equipped with a mechanical agitator, thermometer, addition funnel, and Dean-Stark separator mounted with a reflux condenser. After addition of 31 g of an 18% ammonium acetate in acetic acid solution at room temperature, the mixture was heated to reflux. During reflux at approximately 111°–112° C., the solution became opaque and then solid formed. Total agitation time at reflux was 17 h. After cooling, the solid was filtered and washed with methanol. The solid product, 2-cyano-3-phenyl cinnamamide, was identified by NMR. The yield was 89% (22g), mp 246° C.

Example 8

8.4 g, 0.1 moles of 2-cyanoacetamide, 11.7 g, 0.11 moles benzaldehyde, and 80 g toluene were charged into a flask and ammonium acetate in acetic acid solution added as in Example 7. The slurry formed became light brown under refluxing at 110°–111° C. Total agitation time at reflux was 18 h. After cooling, toluene in the end solution was removed by rotovaporation and the crude solid was washed twice with methanol. The solid product, 2-cyano-cinnamamide was identified by NMR, and collected in 53.5% (9.2 g) yield, mp 129° C.

Example 9

8.4 g, 0.1 mole 2-cyanoacetamide, 13.2, 0.11 moles acetophenone, and 85 g toluene were charged into a flask and ammonium acetate in acetic acid solution added as in Example 7. The resulting slurry became yellow under refluxing at 111° C. Total agitation time at reflux was 18 h. After cooling, two layers of dark liquid were observed and, after few hours, the starting material (4.5 g) was formed in between the layers and removed. Toluene was distilled out from the liquid. A dark, thick liquid containing the product 2-cyano-3-methyl-cinnamamide was identified by NMR.

Example 10

12.5 g, 0.05 mole, hexamethylene bis-cyanoacetamide, 11.6 g, 0.11 moles benzaldehyde, 28.3 g, 18% ammonium acetate solution in acetic acid in 40 g toluene were reacted according to the procedure of Example 1. After drying, 11.5 g hexamethylene bis-2-cyano-cinnamamide were obtained as off-white crystals in 54% yield and the structure was identified by NMR.

Example 11

12.5 g, 0.05 mole, hexamethylene bis-cyanoacetamide, 15.7g, 0.11 moles 4ochlorobenzaldehyde, 28.3 g, 18% ammonium acetate solution in acetic acid in 40 g toluene are reacted according to the procedure of Example 1. After drying, 13.3 g octamethylene bis-(2-cyano)-4'-chlorocinnamamide are obtained as white crystals in 62.1% yield, and the structure is confirmed by NMR.

Example 12

25 g, 0.1 mole, hexamethylene bis-cyanoacetamide, 33.5 g, 0.22 moles 4-methoxyacetophenone, 56 g, 18% ammonium acetate solution in acetic acid in 80 g toluene are reacted according to the procedure of Example 1. After drying, 29.5 g octamethylene bis-(2-cyano-3-methyl)-4'-methoxycinnamamide are obtained as off-white crystals in 57.0% yield, and the structure is determined by NMR.

Example 13

25.0 g, 0.1 mole, hexamethylene bis-cyanoacetamide, 46.5 g, 0.22 moles 4,4'-dimethylbenzophenone, 56 g, 18% ammonium acetate solution in acetic acid in 80 g toluene are reacted according to the procedure of Example 1. After being filtrated and dried, 34.9 g hexamethylene bis-(2-cyano-3, 4"-tolyl)-4'-methylcinnamamide are obtained as white crystals in 54.8% yield, and the structure is confirmed by NMR.

Example 14

25.0 g, 0.1 mole, hexamethylene bis-cyanoacetamide, 48.1 g, 0.22 moles 4,4'-difluorobenzophenone, 56 g, 18% ammonium acetate solution in acetic acid in 80 g toluene were reacted according to the procedure of Example 1. After being filtrated and dried, 11.05 g hexamethylene bis-(2-cyano-3,4"-fluorophenyl)-4'-fluorocinnamamide were obtained as off-white crystals in 17.6% yield, with mp. 250° C. and the structure is confirmed by NMR.

What is claimed is:

1. A process for producing a cyanocinnamamide compound comprising the step of contacting a cyanoacetamide of the formula:

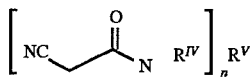

wherein n=1 or 2, and when n=1, $R^{IV}$ is hydrogen and $R^V$ is a $C_1$ to $C_6$ straight chained or branched alkyl, a $C_3$ to $C_7$ cycloalkyl, or a $C_2$ to $C_6$ alkenyl, and when n =2, $R^{IV}$ is hydrogen and $R^V$ is a $C_2$ to $C_{20}$ straight chained or branched alkylene, a $C_3$ to $C_7$ cycloalkylene, or a $C_2$ to $C_{20}$ alkenylene and when $R^{IV}$ is methylene then $R^V$ is an ethylene group forming a six membered ring, with an effective amount of a carbonyl-containing organic compound, a catalytic amount of a condensation catalyst, and a sufficient amount of a solvent under conditions suitable to form a cyanocinnamamide compound.

2. The process of claim 1 wherein the cyanoacetamide is α,ω-hexamethylenebis-cyanoacetamide.

3. The process of claim 1 wherein the carbonyl-containing organic compound is a ketone.

4. The process of claim 3 wherein the ketone is selected from the group consisting of benzophenone, substituted benzophenone, acetophenone, and substituted acetophenone.

5. The process of claim 3 wherein the ketone is benzophenone.

6. The process of claim 1 wherein the carbonyl-containing organic compound is an aldehyde.

7. The process claim 6 wherein the aldehyde is a benzaldehyde or a substituted benzaldehyde.

8. The process of claim 6 wherein the aldehyde is a benzaldehyde.

9. The process of claim 1 wherein the amount of carbonyl-containing organic compound is a molar equivalent ratio of carbonyl-containing compound to cyanoacetamide of from about 1:1 to about 4:1.

10. The process of claim 1 wherein the catalyst is a solution of from about 5 to about 30 percent ammonium acetate in acetic acid.

11. The process of claim 1 wherein the contacting is performed while the cyanoacetamide, carbonyl-containing compound and catalyst are being heated and stirred at reflux for a time of from about 2 to about 30 hours.

12. The process of claim 1 wherein the solvent is toluene, xylenes, or mixtures thereof.

13. The process of claim 1 further comprising synthesizing the cyanoacetamide by the aminolysis of an effective amount of a cyanoacetate ester of the formula:

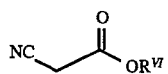

wherein $R^{VI}$ is a $C_1$ to $C_6$ straight or branched alkyl radical with an amine in the presence of a protic or an aprotic solvent.

14. The process of claim 13 wherein the amine is a monoamine of the formula $H_2NR^{VII}$ where $R^{VII}$ is a $C_1$ to $C_6$ straight chained or branched alkyl, $C_3$ to $C_7$ cyclic alkyl or a $C_2$ to $C_6$ alkenyl.

15. The process of claim 13 wherein the amine is a diamine that is piperazine or of the formula $H_2N(R^{VIII})NH_2$ wherein $R^{VIII}$ is a $C_2$ to $C_{20}$ straight chained or branched alkylene, a $C_3$ to $C_7$ cyclic alkylene, or $C_2$ to $C_{20}$ alkenylene radical.

16. The process of claim 13 wherein the amine is α,ω-hexamethylenediamine.

17. The process of claim 13 wherein the aprotic solvent is selected from the group consisting of toluene, xylenes, and mixtures thereof.

18. The process of claim 15 wherein the aprotic solvent is toluene.

19. The process of claim 13 wherein the amount of ester used is from about 1 to about 4 molar equivalents of ester to 1 molar equivalent of amine.

20. A process for producing a cyanocinnamamide compound comprising the step of contacting a cyanoacetamide of the formula:

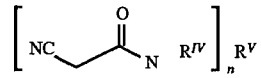

wherein n=1 or 2, and when n=1, $R^{IV}$ is hydrogen and $R^V$ is a $C_1$ to $C_6$ straight chained or branched alkyl, a $C_3$ to $C_7$ cycloalkyl, or a $C_2$ to $C_6$ alkenyl, and when n =2, $R^{IV}$ is hydrogen and $R^V$ is a $C_2$ to $C_{20}$ straight chained or branched alkylene, a $C_3$ to $C_7$ cycloalkylene, or a $C_2$ to $C_{20}$ alkenylene and when $R^{IV}$ is methylene then $R^V$ is an ethylene group forming a six membered ring, with an aldehyde or a ketone in a molar ratio of aldehyde or ketone to cyanoacetamide of from about 1:1 to about 4:1, a catalytic amount of a solution of from about 5 to about 30 percent ammonium acetate in acetic acid, and a sufficient amount of toluene, xylenes, or mixtures thereof, wherein the contacting is performed while the cyanoacetamide, aldehyde or ketone, and ammonium acetate solution are being heated and stirred at reflux for from about 2 to about 30 hours.

21. The process of claim 20 wherein the cyanoacetamide is α,ω-hexamethylene bis-cyanoacetamide.

22. The process of claim 20 wherein the ketone is benzophenone.

23. The process of claim 20 wherein the aldehyde is benzaldehyde.

24. The process of claim 20 wherein the solution of ammonium acetate is an 18 percent ammonium acetate solution.

25. The process of claim 20 further comprising synthesizing the cyanoacetamide by the aminolysis of an effective amount of a cyanoacetate ester of the formula:

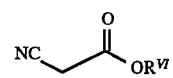

wherein $R^{VI}$ is a $C_1$ to $C_6$ straight or branched alkyl radical with an amine in the presence of an aprotic solvent selected from the group consisting of toluene, xylenes, or mixtures thereof.

26. The process of claim 25 wherein the amine is a monoamine of the formula $H_2NR^{VII}$ where $R^{VII}$ is a $C_1$ to $C_6$ straight chained or branched alkyl, $C_3$ to $C_7$ cyclic alkyl or a $C_2$ to $C_6$ alkenyl.

27. The process of claim 25 wherein the amine is a diamine that is piperazine or of the formula $H_2N(R^{VIII})NH_2$ wherein $R^{VIII}$ is a $C_2$ to $C_{20}$ straight chained or branched alkylene, a $C_3$ to $C_7$ cyclic alkylene, or $C_2$ to $C_{20}$ alkenylene radical.

28. The process of claim 25 wherein the diamine is α,ω-hexamethylenediamine.

29. The process of claim 25 wherein the aprotic solvent is toluene.

30. A process for producing a cyanocinnamamide compound comprising the step of contacting α,ω-hexamethylenebis-cyanoacetamide with a ketone or aldehyde in molar ratio of aldehyde or ketone to cyanoacetamide of from about 1:1 to about 4:1 in the presence of a catalytic amount of a solution of from about 5 to about 30 percent ammonium acetate in acetic acid, and a sufficient amount of solvent, wherein the contacting is performed while the cyanoacetamide, ketone or aldehyde, and ammonium acetate solution are being heated and stirred at reflux for from about 2 to about 30 hours.

31. The process of claim 30 wherein the ketone is benzophenone.

32. The process of claim 30 wherein the aldehyde is benzaldehyde.

33. The process of claim 30 wherein the ammonium acetate solution is a solution of about 18 percent ammonium acetate.

34. The process of claim 30 further comprising synthesizing the cyanoacetamide by the aminolysis of a cyanoacetate ester of the formula:

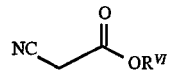

wherein $R^{VI}$ is a $C_1$ to $C_6$ straight or branched alkyl radical with a diamine that is piperazine or of the formula $H_2N(R^{VIII})NH_2$ wherein $R^{VIII}$ is a $C_2$ to $C_{20}$ straight chained or branched alkylene, a $C_3$ to $C_7$ cyclic alkylene, or $C_2$ to $C_{20}$ alkenylene radical in the presence of an aprotic solvent selected from the group consisting of toluene, xylenes, or mixtures thereof, the ester being present in an amount of from about 2 to about 4 molar equivalents to 1 molar equivalent of diamine.

35. The process of claim 34 wherein the diamine is α,ω-hexamethylenediamine.

36. The process of claim 35 wherein the aprotic solvent is toluene.

* * * * *